United States Patent
Bierbaum et al.

(10) Patent No.: US 9,433,475 B2
(45) Date of Patent: Sep. 6, 2016

(54) LASER HANDPIECE, EXCHANGEABLE FIBER-OPTIC INSERT AND CONTROL UNIT THEREFOR

(75) Inventors: Thomas Bierbaum, Bensheim (DE); Siegfried Goisser, Einhausen (DE); Hermann Landgraf, Lorsch (DE); Matthias Rein, Lorsch (DE); Ralf Sutter, Weinheim (DE); Thomas Jerger, Mössingen (DE); Joachim Peuckert, Bönnigheim (DE)

(73) Assignee: SIRONA DENTAL SYSTEMS GMBH, Bensheim (DE)

( * ) Notice: Subject to any disclaimer, the term of this patent is extended or adjusted under 35 U.S.C. 154(b) by 1760 days.

(21) Appl. No.: 12/700,367

(22) Filed: Feb. 4, 2010

(65) Prior Publication Data
US 2010/0216088 A1    Aug. 26, 2010

(30) Foreign Application Priority Data
Feb. 6, 2009 (DE) .......................... 10 2009 000 685

(51) Int. Cl.
| | |
|---|---|
| *A61N 5/06* | (2006.01) |
| *A61C 1/00* | (2006.01) |
| *A61B 18/22* | (2006.01) |
| *A61C 1/18* | (2006.01) |
| *A61B 18/20* | (2006.01) |

(52) U.S. Cl.
CPC ............. *A61C 1/0046* (2013.01); *A61B 18/22* (2013.01); *A61C 1/18* (2013.01); *A61B 2018/202* (2013.01)

(58) Field of Classification Search
USPC .......... 606/15, 16; 607/89, 93; 385/135–137
See application file for complete search history.

(56) References Cited

U.S. PATENT DOCUMENTS

| | | | |
|---|---|---|---|
| 4,457,712 A | 7/1984 | Dragan | |
| 5,221,279 A | 6/1993 | Cook et al. | 606/15 |
| 5,318,562 A | 6/1994 | Levy et al. | 606/16 |
| 5,474,449 A | 12/1995 | Loge et al. | 433/29 |
| 5,851,112 A | 12/1998 | Daikuzono et al. | |
| 5,976,124 A | 11/1999 | Reiser | |
| 6,102,926 A | 8/2000 | Tartaglia et al. | |
| 6,331,178 B1 * | 12/2001 | Loeb et al. | 606/13 |
| 6,997,883 B1 | 2/2006 | Hahn | |
| 7,485,116 B2 * | 2/2009 | Cao | A61B 18/22 606/10 |

(Continued)

FOREIGN PATENT DOCUMENTS

| | | |
|---|---|---|
| DE | 1942987 | 3/1971 |
| DE | 197 14 167 | 10/1998 |

(Continued)

*Primary Examiner* — Tod T Van Roy
(74) *Attorney, Agent, or Firm* — Fitzpatrick, Cella, Harper & Scinto

(57) ABSTRACT

The invention relates to a laser handpiece 1, an exchangeable fiber-optic insert 10, and a control unit 70 therefor. The laser handpiece 1 comprises a optical waveguide 35, which is connected to a light coupling site in a base member 21 and in which the application element 10 for laser light is exchangeably attached to the base member 21. The base member 21 is mounted in a sleeve-type grip 3 for axial displacement therein. The light guide 10 can be wound around a control device 70 which has an annular gap 73 for this purpose and a lower housing part 75 which is offset from an upper housing part 74. An exchangeable fiber-optic insert 10, 27 acting as an application element is provided with a sleeve 80 serving as protection during transportation and as an assembling tool.

8 Claims, 7 Drawing Sheets

(56) References Cited

U.S. PATENT DOCUMENTS

| | | | |
|---|---|---|---|
| 2003/0236517 A1 | 12/2003 | Appling | 606/7 |
| 2005/0154379 A1 | 7/2005 | McGowan et al. | |
| 2007/0191823 A1 | 8/2007 | Scheller | |
| 2008/0181261 A1* | 7/2008 | Boutoussov et al. | 372/6 |
| 2008/0296426 A1* | 12/2008 | Cairns et al. | 242/157 R |
| 2009/0248000 A1 | 10/2009 | Schäfer | 606/13 |

FOREIGN PATENT DOCUMENTS

| | | |
|---|---|---|
| DE | 693 27 187 T2 | 10/2001 |
| DE | 603 02 901 | 8/2006 |
| DE | 10 2006 027 624 A1 | 12/2007 |
| DE | 10 2007 008 115 | 8/2008 |
| EP | 0 553 712 A1 | 8/1993 |
| EP | 1 525 004 | 12/2005 |
| IL | 150914 | 4/2014 |
| WO | WO 2008/092007 A2 | 7/2008 |

\* cited by examiner

LASER HANDPIECE, EXCHANGEABLE FIBER-OPTIC INSERT AND CONTROL UNIT THEREFOR

The invention relates to a laser handpiece, an exchangeable fiber-optic insert, and a control unit for the same. For the treatment of teeth or gums in the oral cavity of a patient, it is known to produce laser light in a laser unit and to guide the same into the patient's mouth and point it toward the site to be treated.

PRIOR ART

Essentially two design forms are known for this purpose. Thus, an up to 3 m long glass fiber is connected at its proximal end to a laser unit and the distal end is used for treatment. After each treatment, the glass fiber is shortened by a defined length for hygienic reasons. When the distance between the laser unit and the patient has fallen short of a minimum value, the remaining glass fiber has to be replaced in its entirety. The handpiece is used for the purpose of guiding the distal end of the glass fiber and is pushed onto the glass fiber and pushed back along the same every time the latter is shortened.

It is further known to connect the laser unit to a handpiece by means of a light guide. Light is transmitted inside the handpiece from the light guide to a glass fiber used for treating the patient. Present-day said glass fibers are disposable and hence they are exchangeably installed in the handpiece.

In both cases, the laser unit and thus the laser beam are activated with the aid of a foot switch, as is common in dental practice.

DE 693 27 187. T2 discloses a laser handpiece, to which laser radiation has from an external laser source to a disposable or consumable optical fiber. This single-use or disposable fiber is connected to the handpiece and the need is eliminated for optical components, particularly lenses, between an optical fiber installed in the handpiece for delivering laser radiation to the handpiece and an exchangeable optical output fiber, since there is additional cooling of the light-transfer parts.

Furthermore, design forms are known in which a finger switch is assigned to the handpiece for activating laser radiation.

For the desirable reuse of the glass fibers, the contaminations on the glass fibers, particularly at the distal end thereof used for treatment, during which it is in physical contact with member tissues over a length of a few millimeters, cannot, as a result of carbonation of said tissues, be removed without causing malfunction of the glass fibers, so that the glass fibers are typically shortened. The disadvantage of said design forms comprising a handpiece mounted for displacement along the glass fiber, particularly in conjunction with an electrical finger switch, is that the length of the glass fiber diminishes from treatment to treatment, while the length of the electrical supply line typically remains constant. Radio transmission of the switch signal would be complicated, since it would require a large amount of space and an energy storage unit. Particular attention must be paid to safety since possible false actuation or failure to switch off the laser will result in considerable risk for the patient, the user, or the assisting staff.

The object of the invention is to provide a laser handpiece comprising a reusable application element, in which the length of the handpiece and the optical and electrical supply lines between the handpiece and the control unit and thus also the ergonomics in the treatment itself remain substantially constant.

A further object is to provide an exchangeable glass fiber which can be easily transported, sterilized and installed.

An additional object of the invention consists in designing a control device for a laser handpiece such that the light guide for supplying laser light to the handpiece can be wound up and stored in a convenient manner.

SUMMARY OF THE INVENTION

These objects are achieved by the features of the independent claims, and preferred developments of the invention are defined in the dependent claims.

A laser handpiece of the invention comprises an optical waveguide which is attached to a light coupling site in a base member, and an application element for laser light that is replaceably attached to the base member. The base member is mounted in a sleeve-type grip for axial displacement therein. The term "optical waveguide" is to be understood herein to mean a supply line from a control device providing laser light, while an "application element" is an element used for treatment with laser light.

The basic concept of a sleeve-type grip comprising a base member mounted for displacement therein allows for the adjustment of the distance of the distal end of the application element—usually a glass fiber—from the distal end of the sleeve-type grip usually formed by a guide cannula, also referred to as a guide tube. This length adjustment is desirable since different applications require different lengths of glass fiber. For example, a free length of the glass fiber of approximately one centimeter is usually sufficient for surgical treatments, while a length of from two to three centimeters is necessary for root-canal treatment. One particular advantage is that the holding position of the laser handpiece in relation to the guide cannula is independent of the length of the glass fiber, and the user can thus always assume the same accustomed position.

Advantageously, the sleeve-type grip can consist of several parts and comprise a finger pad region, a supporting region and an adjusting region. The division of the sleeve-type grip into different components makes for ease of assembly.

In order to assist displacement, the base member can comprise a sliding knob protruding through the sleeve-type grip, and the sleeve-type grip can comprise a slide path with a guide for the sliding knob.

The sliding knob can be moved from a first, restrained position against the force of a spring to a second, displaced position. Accidental displacement of the sliding knob is thus prevented.

Advantageously, a pushbutton for switching on the laser light can be provided on the handpiece, for which purpose the accommodation of the pushbutton in the finger pad region is particularly advantageous. Particularly when a long keypad is provided which extends in the longitudinal direction and the length of which preferably ranges from 20 mm to 45 mm, it is possible to provide different holding positions for the laser handpiece in the longitudinal direction while ensuring actuation of the pushbutton.

The possibility of providing the pushbutton on the base member itself is of particular importance to the invention, since it is then no longer necessary to provide electrical components on the sleeve-type grip itself and the latter can be repeatedly sterilized using, in particular, superheated steam. The pushbutton can be covered by a rotatable lever mounted on the sleeve-type grip, the length of the lever in relation to the swivel axis preferably being at least twice and more preferably from three to five times the actuation distance travelled by the sleeve-type grip for actuation of the pushbutton. The term "actuation distance" refers to the distance to be travelled by the sleeve-type grip to ensure actuation of the pushbutton when the lever acts. This excess distance of the lever in relation to the actuation length ensures that there exist only small differences in the actuating distance or in the actuating force.

The advantage of the special embodiment comprising a lever acting on the pushbutton is that the pushbutton or, if more are provided, the pushbuttons can be actuated with almost the same force over the entire displacement path. It is thus possible to provide a large keypad and ensure the actuation of the pushbuttons in any position of the base member relative to the sleeve.

The pushbutton on the base member can be secured against accidental actuation after the sleeve has been removed. For this purpose, the pushbutton can be disposed, for example, in a depression on the base member or raised areas can be provided in the immediate vicinity of the pushbutton.

Accidental actuation of the pushbutton by the user is regarded as not possible in the prior art when the design is such that the standard test finger specified in the relevant standard IEC 60601-1 cannot effect actuation. A mechanical safeguard for the pushbutton can take the form of raised areas, preferably consisting of side ridges extending in the longitudinal direction, the height thereof in relation to the pushbuttons and the spacing thereof preventing any actuation of the pushbutton by a standard test finger.

For the purpose of switching on the laser light, the pushbutton can be connected to an evaluating unit, for example, by means of an electric circuit or a signal line which can also transmit optical signals.

A number of redundant pushbuttons can be provided for increasing operational reliability.

In a development of the invention, the base member comprises a sensor which is oriented toward the optical path in the base member and which detects light having the wavelength of the light supplied via the light guide, and which, as also in the case of the pushbuttons, can transmit a signal to an evaluating unit present in the laser handpiece or in a control unit. Particularly during operation with an exchangeable fiber-optic insert, the detection of the presence of this exchangeable fiber-optic insert by means of a sensor increases the safety of operation of the laser handpiece. Furthermore, a fracture of the glass fiber in the interior of the sleeve-type grip can also be detected.

A number of redundant sensors can be provided for increasing operational safety.

The laser handpiece can comprise an exchangeable application element for laser light, whose proximal end remote from the treatment end is connected to a light coupling site in the base member. In particular, the application element can be an exchangeable fiber-optic insert.

This exchangeable fiber-optic insert can be sterilizable and the parts coming into contact with the patient can likewise be sterilizable. Naturally, automated processes for cleaning, disinfection, and sterilization can also be used for completing the necessary measures. The provision of exchangeable fiber-optic inserts reduces treatment costs, and ensures that the actual length of the handpiece is always the same. In spite of the necessity for shortening the glass fiber due to wear or contamination due to burned-in tissue, the glass fiber can be used a number of times, since the shortened length can be compensated.

Advantageously, the light guide can be accommodated in a handpiece hose, which is connected to the base member and is freely movable in relation to the sleeve-type grip. Furthermore, an electric supply line pertaining to the electric circuit or other lines such as optical signal lines can be provided that pass together with the light guide to a control device.

Another object of the invention is an exchangeable fiber-optic insert for a laser handpiece, which fiber-optic insert comprises a connecting piece disposed at one end for connection to the laser handpiece and a glass fiber extending away from the connecting piece and comprising a treatment end remote from the connecting piece, the connecting piece comprising a region for the introduction and transfer of a torque to an additional retaining region. Furthermore, a sleeve surrounding the glass fiber is provided, which sleeve can be fitted on the torque-transferring region of the connecting piece and the end of which comprises a connecting region that cooperates with the torque-transferring region of the connecting piece.

The slip-on sleeve also molded as a tool serves on the one hand as transport protection for the glass fiber and also as a tool for screwing the exchangeable fiber-optic insert into the laser handpiece and as a container for the glass fiber during sterilization.

Yet another object of the invention relates to a control device for a laser handpiece, comprising an optical waveguide connected to the control device. The housing has an annular gap which extends on the peripheral side and at least optically divides the housing into a lower housing half and an upper housing half, which protrudes laterally beyond the lower housing half, when regarded from the front, while the lower housing half protrudes at the rear laterally beyond the upper housing half, when viewed from the front.

The supply line to the handpiece is thus easy to handle in spite of a length of approximately two meters. The different spatial conditions in a dental practice can be taken into consideration in that the user need not unwind the entire length of the supply line to the handpiece.

The light guide can be disposed in a handpiece hose connected to the control device. A signal line or a control line can be additionally provided in the handpiece hose in order to enable a signal to be transmitted from the laser handpiece to the control device.

Advantageously, the width of the annular gap can be equal to at least one diameter of the light guide or the handpiece hose but less than two diameters and preferably less than 1.2 diameters to make controlled winding possible.

Preferably, the light guide can pass from the housing interior without buckling to the base of the annular gap.

According to a development of the invention, the light guide or the handpiece hose can comprise electrical and/or optical connections and it can be removed from the control device for maintenance purposes.

Furthermore, retaining means in the form of a mechanical stopper, a hook and loop fastener, or a magnetic retainer can be provided in the annular gap.

A storage device for the handpiece can be provided on the housing itself, in which case it will be possible, particularly when a laser handpiece as described above is used, to carry out a length adjustment of the light guide or handpiece hose when the handpiece is located in the storage area.

BRIEF DESCRIPTION OF THE DRAWINGS

An exemplary embodiment of the invention is shown in the drawings, in which:

FIG. 1 is a perspective view of a laser handpiece of the invention for dental usage. The laser handpiece 1 comprises a handpiece hose 2 comprising a light guide (not shown) and optionally electrical transmission lines (not shown), the handpiece hose 2 being guided in a sleeve-type grip 3. The sleeve-type grip 3 can consist of a number of parts and comprises a finger pad region 4, a supporting region 5 and an adjusting region 6 disposed in line when regarded in the longitudinal direction. A tip 7 comprising a guide tube 8 and a connecting part 9 for connection to the sleeve-type grip 3 are provided at that end of the sleeve-type grip 3 that is remote from the handpiece hose 2. An application element for laser light in the form of a glass fiber 10, by means of which laser light is guided to the treatment site, emerges from the guide tube 8 of the tip 7. Such glass fibers are known for the treatment of soft and hard tissue. After each use of the laser handpiece it may be necessary to shorten the glass fiber 10 in order to remove tissue residues burnt into the glass fiber 10 during treatment.

Furthermore, it is evident from FIG. 1 that the sleeve-type grip 3 comprises a keypad 11 in the finger pad region 4, which keypad extends parallel to the longitudinal axis of the laser handpiece and makes it possible to actuate a pushbutton that is located thereunder, as explained below. This keypad 11 is between 20 and 45 mm long and enables activation of the pushbutton located thereunder independently of the actual size thereof both during treatment of front teeth, in which case the laser handpiece is gripped toward the front, and during treatment of molars, in which case the laser handpiece is gripped nearer its rear end.

Figure 1:
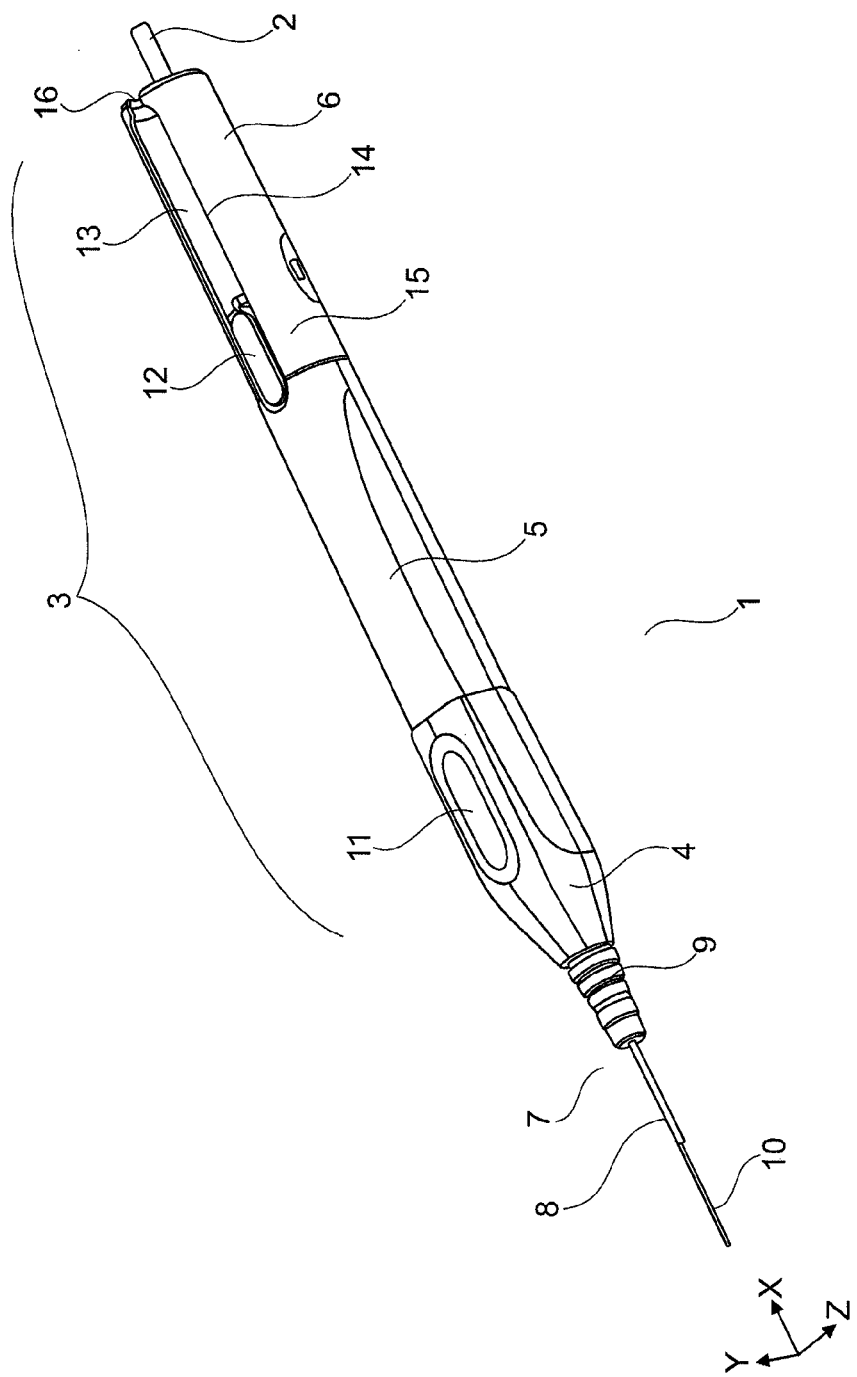
FIG. 1 is a perspective view of the laser handpiece of the invention.

Furthermore, a sliding knob 12, which is disposed in a recess 13 in the adjusting region 6 of the sleeve-type grip 3, is shown in FIG. 1, the sleeve-type grip comprising a slide path 14 displaying a guide for the sliding knob 12. The sliding knob 12 is mounted on a base member (not shown in the figure), which is disposed inside the sleeve-type grip 3, said base member being displaceable longitudinally along the slide path 14 in the sleeve-type grip 3 by means of the sliding knob 12. The cooperation between the sliding knob 12 and the slide path 14 prevents rotation in relation to the grip sleeve.

The adjusting region 6 of the sleeve-type grip 3 is formed as a separate component in the form of an end sleeve 15 and it comprises an end recess 16, which is disposed in the region of the recess 13 and is connected to the same and into which the handpiece hose 2 can be inserted.

Figure 2:
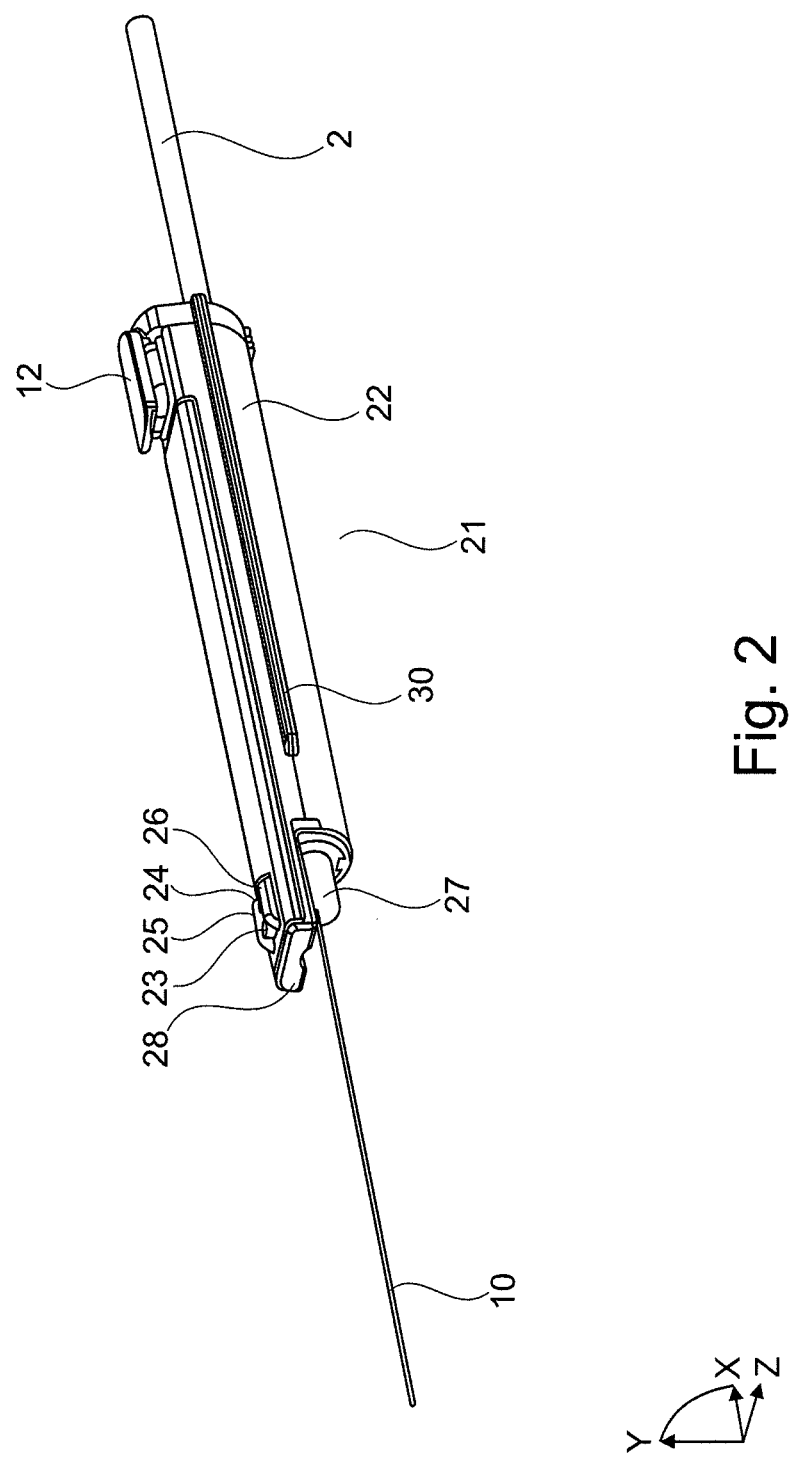
FIG. 2 shows a displaceable base member disposed inside the laser handpiece shown in FIG. 1.

FIG. 2 shows the aforementioned base member 21, which is disposed inside the sleeve-type grip 3 shown in FIG. 1 and at the end of which oriented toward the handpiece hose 2 the sliding knob 12 is provided and at the opposite end of which the glass fiber 10 is disposed. The sliding knob 12 is disposed on the top surface of the housing 22 of the base member 21. Likewise, two pushbuttons 23, 24 are provided, which are offset in relation to each other, when regarded in the longitudinal direction, and which are kept from being accidentally actuated by laterally disposed ridges 25, 26. The height and spacing of the ridges 25, 26 are such that the standard test finger specified in the relevant IEC 60601-1 standard cannot cause accidental actuation of the pushbuttons.

The glass fiber 10 disposed on the base member 21 comprises a connecting piece 27, also referred to as a ferrule, which can be releasably mounted in the housing 22 for example by way of a screw thread in order to make it possible to replace the glass fiber 10 when it becomes worn or fractured. The glass fiber 10 and the connecting piece 27 together form the exchangeable fiber-optic insert. The top side of the housing 22 projects beyond this connecting piece 27 toward the front so that a sensor for detecting the presence of the exchangeable fiber-optic insert, can be provided on that side of the housing projection 28 that is oriented toward the connecting piece 27. The presence of the exchangeable fiber-optic insert is detected, for example, by detection of light in the wavelength range of a guiding laser beam or of the treatment laser beam, in that the intensity of these wavelengths is detected as a signal, for example.

The base member can alternatively be guided in the sleeve-type grip by means of additional grooves and cams, of which here a longitudinally extending cam 30 can be seen on the base member.

Figure 3:
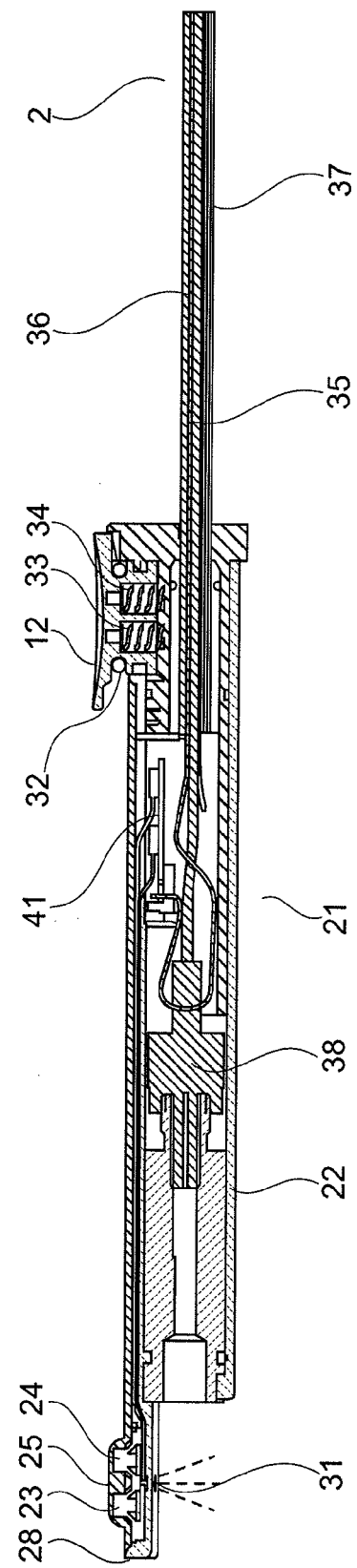
FIG. 3 is a section of the base member shown in FIG. 2.

FIG. 3 shows a longitudinal section of the base member shown in FIG. 2, the exchangeable fiber-optic insert being omitted. For this reason, a sensor 31 disposed on the bottom surface of the projection 28 will deliver an error signal when laser beams emerge from the housing 22 of the base member 21.

The base member 21 is provided with the sliding knob 12, which is disposed on the upper side of the housing 22 and is mounted such that it can be pressed down in relation to the housing 22 against the force of a spring and which comprises a circumferential O-ring 32, which cooperates with the slide path of the sleeve-type grip shown in FIG. 1 for the purpose of blocking movement thereof. By pushing down the sliding knob 12, the O-ring 32 is released relatively to the slide path so that displacement is allowed. When the sliding knob 12 is released, it is pushed by resilient elements 33, 34 against the slide path on the housing 22.

In the region of the sliding knob 12, the handpiece hose 2 also enters the housing 22 and is held there with the aid of a strain relief. The handpiece hose 2 comprises firstly a light guide 35 and secondly transmission lines 36, the light guide 35 and the transmission lines 36 being enclosed by common sheathing 37. The transmission lines 36 can be signal or control transmission lines; additional optical waveguides for signal transmission can also be present.

In the interior of the housing 22, the light guide 35 passes to an optical light injector 38 and it emerges from the optical light injector 38, which can also contain optical components, toward the application element.

The housing 22 further comprises a printed circuit board 41, to which the electrical transmission lines 36 are connected and which is electrically connected to the pushbuttons 23, 24 and the sensor 31. An evaluating unit can also be provided on the printed circuit board 41 in order to evaluate the electrical signals originating from the pushbuttons 23, 24 and the sensor 31 and to allow or prevent the flow of laser light through the control unit. The printed circuit board 41 can also be used solely for forwarding signals to the control device if the evaluating unit is accommodated therein. The signals can be transmitted electrically or optically.

The housing 22 of the base member is hermetically sealed off from the environment.

Figure 4:
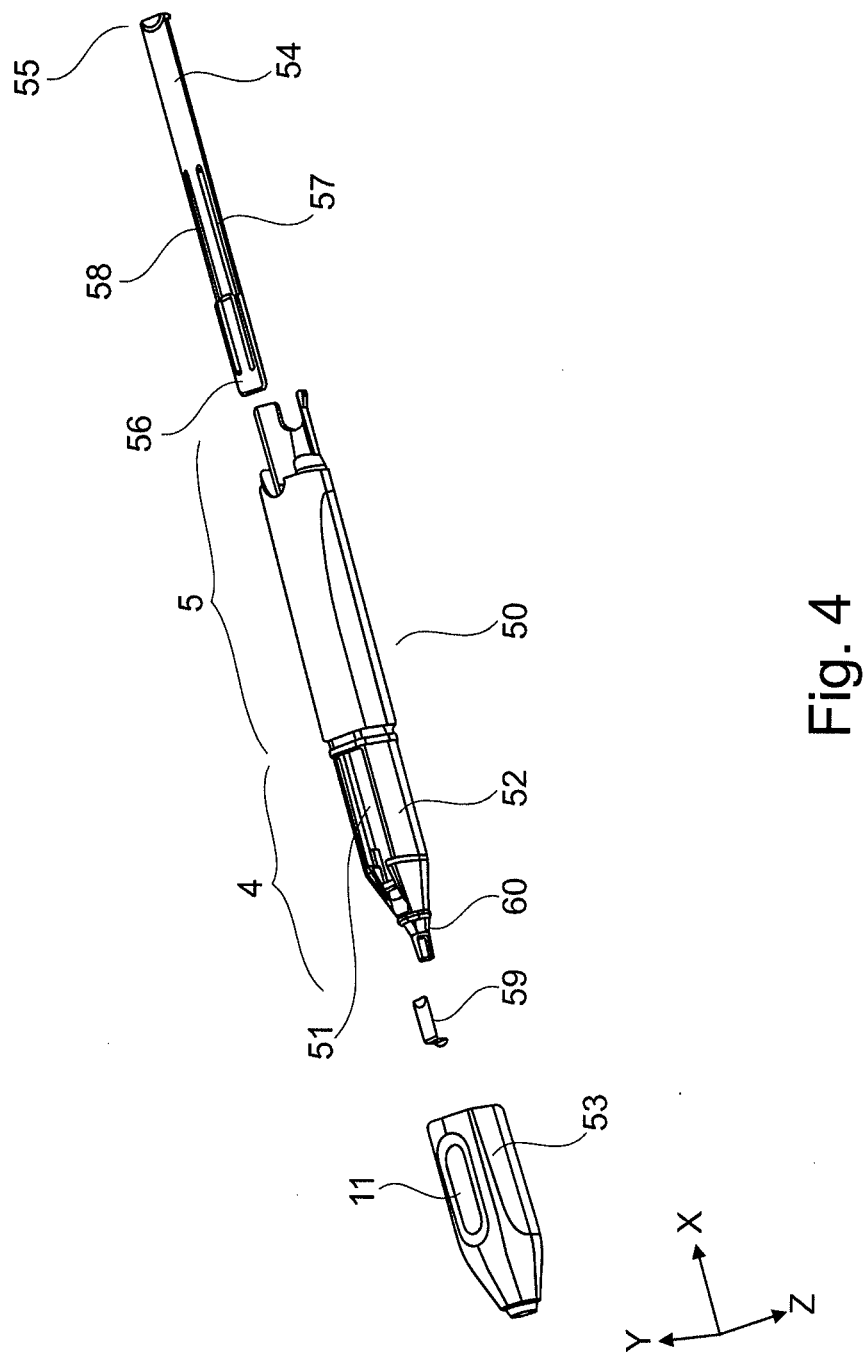
FIG. 4 is an exploded view of a sleeve-type grip of the laser handpiece shown in FIG. 1.

FIG. 4 is an exploded view of the sleeve-type grip 3 comprising the finger pad region 4 and supporting region 5, a recess 51 being provided in the finger pad region 4 on the sleeve member 50, by means of which recess the pushbuttons on the base member (not shown) shown in FIG. 2 can be actuated. For this purpose, the front end 52 of the sleeve member 50 comprises, on the one hand, a removable cover 53 having a deformable keypad 11. On the other hand, a lever 54 is provided which extends into the interior of the sleeve member 50 and covers the recess 51. After assembly, the lever 54 is mounted in the sleeve member 50 with the aid of a swivel joint 55 and the front end 56 thereof is located completely underneath the keypad 11. To ensure that the lever is pressed down on the pushbuttons of the base member shown in FIG. 2, longitudinal grooves 57, 58 are provided, the width of which is such that safety ridges 25, 26 shown in FIG. 2 can engage at that point.

In order to bring the lever 54 securely into the raised end position, a resilient element 59 is further provided which is held in the front part 52 and is connected to the lever 55. This resilient element 59 is not strictly necessary, but it additionally ensures resetting of the lever 54 over and above the reset effected by the pushbuttons themselves.

The end of the front part 52 is formed as a Luer connector so that a standard connection 60 can be used for attaching the exchangeable tip 7 (not shown) shown in FIG. 1. Such connectors are known from the prior art relating to the medical field.

Figure 5:
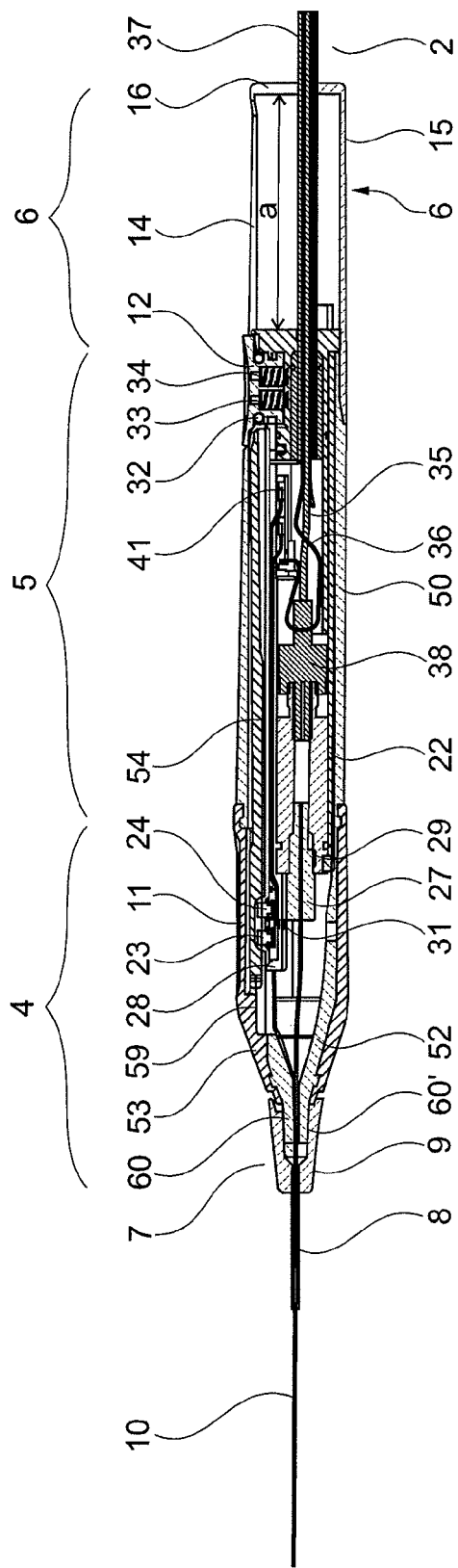
FIG. 5 is a longitudinal section of the laser handpiece shown in FIG. 1.

FIG. 5 is a longitudinal view of the assembled laser handpiece shown in FIGS. 1 to 4. The guide tube 8 of the tip 7 is permanently held in the connecting part 9, and the connecting part 9 is formed with a Luer connector 60' at the front end 52 of the sleeve member 50 shown in FIG. 4, which front end likewise comprises a corresponding Luer standard connector 60.

In the inserted state of the glass fiber, the guide tube 8 can be bent with the aid of a bending tool without damaging the inserted glass fiber. However, this bending is irreversible. Furthermore, it is not possible to push the glass fiber 10 through the tip 7 if the guide tube 8 is in a bent state.

The additional components illustrated correspond to those shown in FIGS. 1 to 4. It should be pointed out here that the glass fiber 10 is brought into a maximum advanced end position of the housing 22 of the base member in relation to the sleeve member 50 and it thus protrudes beyond the guide tube by the maximum distance. When the housing 22 of the base member is pushed back into the end sleeve 15 by means of the sliding knob 12 pressed down for this purpose, the housing 22 can cover an adjusting distance 'a'. Due to the recess 16 at that end of the end piece 15 which is near the hose, the handpiece hose 2 is pushed out of the laser handpiece by this distance 'a'.

This sectional representation also shows the sensor 31, which is disposed on the lower side of the projection 28 and is oriented toward the exchangeable fiber-optic insert comprising the glass fiber 10 and the connecting piece 27 and which is used for detecting laser radiation and is electrically connected to the printed circuit board 41.

Figure 6:
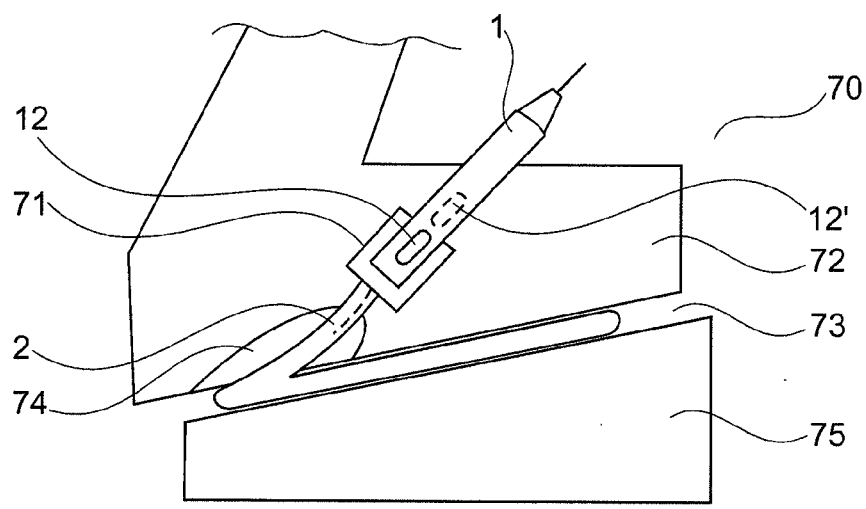
FIG. 6 is a side-view of a control device for the laser handpiece shown in FIG. 1.

FIG. 6 shows a control device for regulating the supply to the laser handpiece described above, the laser handpiece 1 being held in a storage region 71 on a housing part 72. The handpiece hose 2 is inserted in an annular gap 73 and it leaves this annular gap 73 just before the storage region 71. In order to prevent bending, the housing part 72 can include a depression 74. The length of hose 2 emerging from the annular gap 73 can be tensioned by a movement of the sliding knob 12 on the laser handpiece 1 to a position 12' such that the handpiece hose 2 does not fall out of the annular gap 73, including when the control device 70 is being transported.

It can be seen shown in FIG. 6 that the upper housing part 72 of the control device 70 is offset in relation to the lower housing part 75, and the upper housing part 72 on the right of the control unit oriented toward the user in the side-view shown, that is to say, on the left-hand side of the drawing, protrudes beyond the lower housing part 75, whereas on the side remote from the user, that is to say, on the right-hand side of the drawing, the lower housing part 75 protrudes beyond the upper housing part 72. This is achieved, for example, when a cylinder is cross cut and the two cylindrical parts are offset in relation to each other. The advantage of this particular embodiment of the housing of the control device is that, when winding up the handpiece hose 2, it can be fitted on the lower housing part 75 in that region of the control device that is remote from the user, whereas the handpiece hose, on that side of the control device that is near the user, passes underneath the upper housing half and into the circumferential annular gap 73 when being guided around said control device and is thus wound up.

Figure 7:
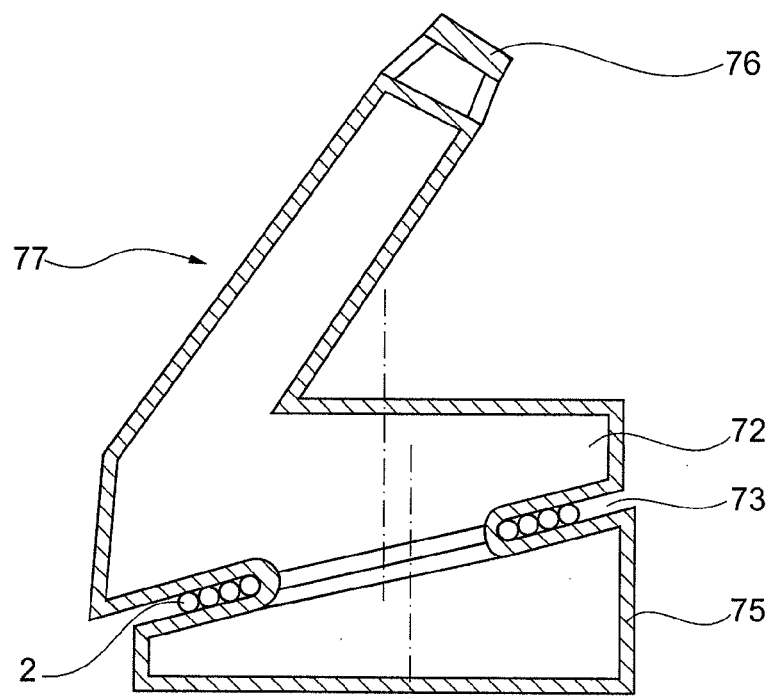
FIG. 7 is a diagrammatic section of the control device shown in FIG. 6.

It is clear from the diagrammatic cross section shown in FIG. 7 that the handpiece hose 2 is spirally wound in the annular gap 73 such that each winding of the hose rests against the preceding winding. When tightly wound up, the handpiece hose 2 is therefore always stored in the same position in the annular gap 73, and that end of the handpiece stored in the storage region 71, as shown in FIG. 5 that protrudes from the annular gap 73 always has the same length.

A display device, formed in this case as a console 77, can be mounted on the housing part 72. Likewise, input means (not shown) such as keys or a control dial can be provided in order to control a device (not shown) disposed in the interior of the housing for the purpose of providing the laser beams. Furthermore, a handle 76 can be provided above the console 77 to ensure that the control device can be easily transported.

Figure 8:
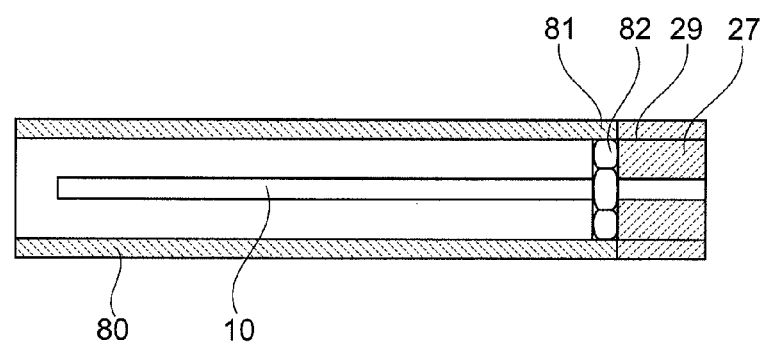
FIG. 8 shows an exchangeable fiber-optic insert with a storage tube.

FIG. 8 shows an exchangeable fiber-optic insert 10, which is attached to the connecting piece 27, and the connecting piece 27 has a retaining region provided with a male thread 29, and these parts are together also referred to as an exchangeable fiber tip. A bayonet lock or any other attachment means for producing a connection by turning the connecting piece 27 can alternatively be provided on the retaining region instead of a male thread 29.

In order to make it possible to attach the connecting piece 27 without damaging the glass fiber 10, for example, by screwing or turning the same, a slip-on sleeve 80 is provided which surrounds the glass fiber 10 and has a connecting region 81 leading to a torque-transferring region 82 on the connecting piece 27. The torque-transferring region 82 can be a kind of hexagonal nut for a socket wrench, or more preferably a connection comprising only punctiform bearing surfaces, for example, a unilateral flattened portion or a pin mounted at right angles to the longitudinal axis, for example. A rotationally symmetrical torque-transferring region designed for being screwed tightly by friction lock can also be used. The preferred solution is that which provides the possibility of limiting the torque in a simple manner when screwing the torque-transferring region tightly.

The slip-on sleeve 80 also having the form of a tool serves as a transport protector for the glass fiber, as a tool for screwing the exchangeable fiber-optic insert into the base member 21 shown in FIG. 2 and as a container for the glass fiber during sterilization.

Figures 9A, 9B, 9C:
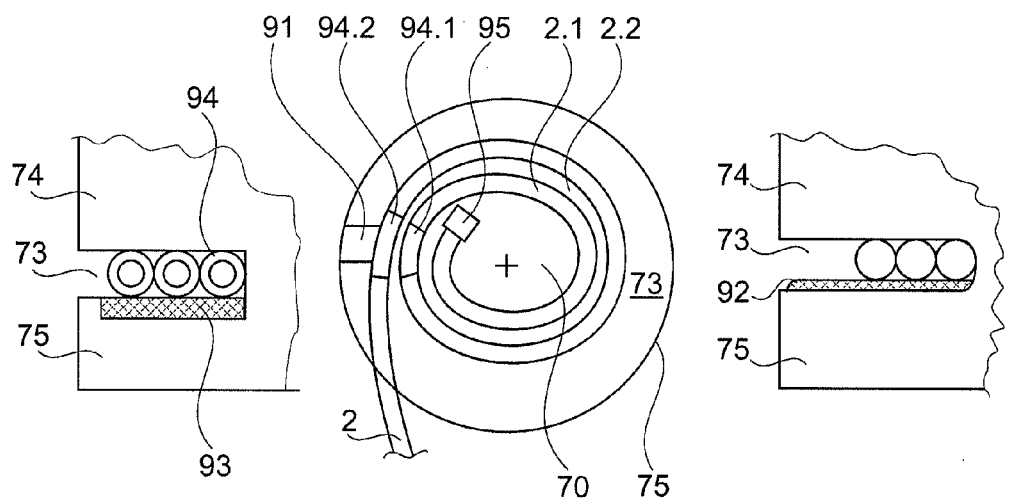
FIG. 9A shows an embodiment of the cable rewinding means of the control device shown in FIG. 6.
FIG. 9B shows a cable locking device incorporating a mechanical lock.
FIG. 9C shows a magnetic cable locking device.

FIGS. 9A to 9C show various restraining means that enable the handpiece hose 2 to be unwound winding by winding. Firstly, FIG. 9A shows two windings 2.1, 2.2 of the handpiece hose 2 wound up in the annular gap 73 of the control device 70 provided in the housing, a retaining element 91 being provided in the 9 o'clock position. This holding element 91 prevents accidental loosening of the wound up windings 2.1, 2.2 of the handpiece hose 2. This can be achieved by providing a silicone bead or an elastic support 92 as a retaining element 91 in the annular gap 73 between the upper and lower housing parts 74, 75. Alternatively, as shown in FIG. 9C, a magnet 93 disposed below the annular gap 73 in the lower housing part 75 can be provided as the retaining element to cooperate with a magnetic sleeve 94 on the handpiece hose 2, shown in FIG. 9A as hose sleeves 94.1 and 94.2.

A hook and loop fastener can be alternatively provided in place of the magnet and the sleeves.

The light guide or the handpiece hose passes from the interior of the control device 70 into the annular gap 73 without buckling and is connected to the control device 70 by means of a connector 95. The optical waveguide 35 or the handpiece hose 2 can be removed from the control device by means of the connector 95 for purposes of repair and maintenance.

REFERENCE SIGNS

1 laser handpiece
2 handpiece hose
2.1 winding
2.2 winding
3 sleeve-type grip
4 finger pad region
5 supporting region
6 adjustment range
7 tip
8 guide tube
9 connector
10 glass fiber—application element
11 keypad
12, 12' sliding knob
13 recess
14 slide path
15 end sleeve
16 recess
21 base member
22 housing
23 pushbutton
24 pushbutton
25 ridge/safety ridge
26 ridge/safety ridge
27 connecting piece
28 projection
29 male thread/retaining region
30 cam
31 sensor
32 O-ring
33 resilient element
34 resilient element
35 optical waveguide
36 line/signal line/control line
37 sheathing
38 light injector
41 printed circuit board/evaluation unit
50 sleeve member
51 recess/clearance
52 front end/front part
53 cover
54 lever
55 swivel joint/lever
56 front end
57 longitudinal groove
58 longitudinal groove
59 resilient element
60 standard Luer connection on the housing
60' Luer connection on the tip
70 control device
71 storage region
72 housing part
73 annular gap
74 depression
75 lower part/housing part
76 handle
77 console
80 slip-on sleeve
81 connecting region
82 torque-transferring region
83 retaining region
91 retaining element
92 support
93 magnet
94 collar
94.1 hose collar
94.2 hose collar
95 connection for optical waveguide/hand piece hose
'a' slide path

The invention claimed is:

1. A control device for a laser handpiece, comprising:
   an optical waveguide;
   a housing including a peripherally extending annular gap that divides the housing into at least a lower housing portion and an upper housing portion,
   wherein the lower housing portion is connected to the upper housing portion,
   wherein the optical waveguide is disposed in the annular gap between at least part of the lower housing portion and at least part of the upper housing portion and emerges from an interior of the housing,
   wherein the waveguide can be wound up in the annular gap, and
   wherein the optical waveguide leaves the interior of the housing and is guided to a base of the annular gap without buckling.

2. The control device as defined in claim 1, wherein the optical waveguide is disposed in a handpiece hose connected to the control device, and a signal line or a control line also is disposed in the handpiece hose.

3. The control device as defined in claim 2, wherein a width of the annular gap is at least equal to a diameter of one of the optical waveguide and the handpiece hose and is less than two times the diameter of the one of the optical waveguide and the handpiece hose.

4. The control device as defined in claim 2, wherein the optical waveguide or the handpiece hose includes at least one of an electrical and an optical connector and can be removed from the control device for maintenance purposes.

5. The control device as defined in claim 1, wherein at least one of a mechanical stopper, a hook, a loop fastener, and a magnetic retainer is provided in the annular gap.

6. The control device as defined in claim 1, wherein the housing is provided with a storage device for the handpiece.

7. The control device as defined in claim 6, further comprising the laser handpiece, wherein the optical waveguide is fixed to a light coupling site in a base member of the laser handpiece, an application element for laser light is attached to the base member, and the base member is mounted in a sleeve-type grip for axial displacement therein.

8. The control device as defined in claim 1, wherein the upper housing portion, when viewed from the front, projects laterally beyond the lower housing portion, and the lower housing portion, when viewed from the front, projects at the rear laterally beyond the upper housing portion.

* * * * *